(12) United States Patent
Cuní Bravo et al.

(10) Patent No.: US 9,062,215 B2
(45) Date of Patent: Jun. 23, 2015

(54) PAINT BINDER COMPOSITION

(76) Inventors: Jorge Cuní Bravo, Madrid (ES); Pedro Cuní Bravo, New York, NY (US); Montserrat Cuní Bravo, Madrid (ES)

(*) Notice: Subject to any disclaimer, the term of this patent is extended or adjusted under 35 U.S.C. 154(b) by 0 days.

(21) Appl. No.: 14/116,740

(22) PCT Filed: May 9, 2012

(86) PCT No.: PCT/ES2012/070325
§ 371 (c)(1),
(2), (4) Date: Jan. 15, 2014

(87) PCT Pub. No.: WO2012/152973
PCT Pub. Date: Nov. 15, 2012

(65) Prior Publication Data
US 2014/0121311 A1    May 1, 2014

(30) Foreign Application Priority Data
May 9, 2011   (ES) .................... 201130738

(51) Int. Cl.
| | | |
|---|---|---|
| C09D 7/12 | (2006.01) | |
| A61M 31/00 | (2006.01) | |
| C09D 11/00 | (2014.01) | |
| C09D 191/06 | (2006.01) | |
| C09D 11/06 | (2006.01) | |
| C09D 11/12 | (2006.01) | |
| C09D 5/02 | (2006.01) | |
| C08K 5/09 | (2006.01) | |
| C08K 5/101 | (2006.01) | |

(52) U.S. Cl.
CPC ............ C09D 7/1208 (2013.01); A61M 31/007 (2013.01); C09D 11/00 (2013.01); C09D 191/06 (2013.01); C09D 11/06 (2013.01); C09D 11/12 (2013.01); C09D 5/022 (2013.01); C09D 7/1233 (2013.01); C08K 5/09 (2013.01); C08K 5/101 (2013.01)

(58) Field of Classification Search
CPC ........ C09D 7/12; C09D 11/00; C09D 191/06; A61M 31/00
USPC .................................................. 524/322, 276
See application file for complete search history.

(56) References Cited

U.S. PATENT DOCUMENTS

| | | | |
|---|---|---|---|
| 6,933,014 B1 * | 8/2005 | Wynne .................... | 427/272 |
| 2011/0098397 A1 | 4/2011 | Plehiers et al. | |

FOREIGN PATENT DOCUMENTS

| | | |
|---|---|---|
| EP | 0750026 | 12/1996 |
| ES | 2073308 | 1/1993 |
| ES | 2099480 | 10/1993 |
| JP | 53139717 | 12/1978 |
| WO | WO 02/04004 | 1/2002 |
| WO | WO 0204004 A1 * | 1/2002 |

OTHER PUBLICATIONS

International Search Report; PCT Application No. PCT/ES2012/070325; Aug. 9, 2012.

* cited by examiner

*Primary Examiner* — Michael M Bernshteyn
(74) *Attorney, Agent, or Firm* — Blakely Sokoloff Taylor & Zafman LLP

(57) ABSTRACT

The present invention relates to composition and use of a binder for the production of paints and inks. Said binder comprises the following elements: waxes, emulsifying agents, curing agents, drying oils, resins, metal ions and water. Furthermore, the present invention discloses a process for the preparation of binder compositions and paints containing them.

14 Claims, No Drawings

PAINT BINDER COMPOSITION

The present application is a non-provisional application of International Application No. PCT/ES2012/070325, filed May 9, 2012.

The present invention relates to composition and use of a binder for the production of paints. Such a binder comprises the following elements: waxes, emulsifying agents, curing agents, resins, glycerol, metal ions and water. Furthermore, in the present invention, a process for the preparation of binder compositions and the paints that contain them is described.

The invention is comprised within the field of paints and inks, in particular the creation of new chemical formulations with binding properties for use in painting techniques for artists, from use in schools to inks for woodcut printing, screen printing, lithography, and etching, or for decorative painting on walls, both exterior and interior.

BACKGROUND OF THE INVENTION

Current artistic paintings of highest quality and versatility use basically two types of binders: drying oils in oil paints, and binders based on acrylic resins in acrylic paints.

Drying oils present two problems for the artist: the slow drying of the paint, and the use of toxic organic solvents in order to adjust the viscosity and transparency of the paint.

Acrylic resins present problems of loss of volume during drying and lack of transparency of the pictorial layer.

These drawbacks in conventional paints require the development of new binders that will solve the problems set forth above, in order to obtain paints with a fast drying time which do not require organic solvents and present no loss of volume during drying.

DESCRIPTION OF THE INVENTION

The present invention relates to a composition with binding properties and its use for paints and inks, comprising the following advantages over the binder compositions already known in the state of the art:

When the binder is part of oil paints:
Quick drying, allowing one to paint over lower layers of paint during a single session.
Lack of differences in finish between diluted and thick brushstrokes. In oil paints, thick brushstrokes are brighter than diluted brushstrokes, so that paintings require varnishing in order to obtain an homogeneous finish.
Absence of toxic solvents, since oil paints require the use of organic solvents in order to adjust their viscosity.
Ease of cleaning of brushes and implements, which can be done with soap and water instead of VOC (volatile organic compounds).
Paint can be applied on paper without priming, as needed in oil paints.

When the binder is part of acrylic paints:
Possibility to apply thick brushstrokes which do not lose volume. In acrylic paints, thick empastoes show a significant loss of volume during drying.
Unlike with acrylic paints, colours do not change during drying, allowing the painter full control over the final result of the painting.
Diluted brushstrokes show higher transparency and body, providing superior visual strength.
Greater durability.

When the binder is part of oil or acrylic paints:
The outstanding optical qualities of beeswax provide bright and intense colours, and a satin finish with waxy lustre, highly pleasing to the eye, very different from oils and acrylics, allowing artists to achieve new plastic effects.

Hence, a first aspect of the present invention relates to a paint binder composition comprising the following elements:
waxes;
emulsifying agents;
curing agents;
drying oils;
resins;
polyvalent metal ions; and
water.

According to a preferred embodiment, the waxes are selected from the group consisting of waxes of vegetable, animal, mineral or synthetic origin.

According to another preferred embodiment, the waxes are selected from the group consisting of: candelilla wax, ouricuri wax, sugarcane wax and carnauba, spermaceti, beeswax, lanolin wax, Chinese wax, ceresin, montan wax, ozokerite, paraffin waxes, microcrystalline waxes, polyethylene waxes, halogenated hydrocarbon waxes, alkyl ester or polyhydric alcohol waxes, hydrogenated waxes, ketones, amides of fatty acids, or any combination thereof.

Preferably, the waxes are selected from the group consisting of beeswax, carnauba, ceresin, and microcrystalline waxes. Beeswax is the most preferred.

According to another preferred embodiment, the waxes are in a weight percentage of between 20 and 55% of the total composition. Even more preferably, waxes are in a weight percentage of between 33 and 50% of the total composition.

According to another preferred embodiment, the emulsifiers are selected from the group consisting of potassium salts of fatty acids, potassium soaps composed of fatty acids with or without glycerol content, anionic surfactants such as alkyl sulfates, alkyl ether sulphates, sulfated alkanolamides, sulfated diglycerides, sulfonates, surfactants, organophosphate surfactants, sarcosides, nonionic surfactants, or any combination thereof. Preferably, the emulsifiers are selected from potassium oleate and potassium linoleate.

According to a preferred embodiment, the fatty acids of the potassium soaps of are selected from oleic, linoleic, linolenic, or a combination thereof. Preferably these fatty acids are in a weight percentage higher than 40% of the emulsifier.

According to another preferred embodiment, the emulsifying agents are in a weight percentage of 2 to 45% of the total composition. Preferably they are in a weight percentage of 15 to 25%, and even more preferably in a weight percentage of 19% of the total composition.

According to a preferred embodiment, the curing agents are selected from the group consisting of metal soaps such as calcium oleate; aluminium stearate; barium stearate; magnesium palmitate; metal resinates such as zinc, calcium, manganese resinates; calcium, barium, zinc, magnesium oxalates; calcium, zinc, barium naphthenates and octoates; calcium, aluminium oleate or stearate; or any combination thereof.

According to another preferred embodiment, the curing agents are in a percentage less than or equal to 25% of the total composition. Preferably, they are in a weight percentage of 6% of the total composition.

According to another preferred embodiment, the drying oils are selected from the group consisting of linseed, walnut, poppyseed, perilla, tung, soybean, oiticica, lumbang, sunflower, hemp, safflower, stillingia, tobacco seed oils.

According to another preferred embodiment, drying oils are in a weight percentage not exceeding 20% with respect to the total composition. Preferably they are in a weight percentage of 6% of the total composition.

According to another preferred embodiment, the resins are selected from the group consisting of synthetic or natural resins, or any combination thereof. Preferably, the resins are selected from the group consisting of acrylic resins, alkyd resins, dammar, mastic, copal, shellac, sandarac, rosin, or any combination thereof. Even more preferred resins are selected from acrylic and dammar.

According to another preferred embodiment, the resins are in emulsion; in dispersion; dissolved in organic solvents, preferably turpentine, white spirit or toluene; dissolved in drying oils, preferably linseed oil, walnut oil, poppy oil or safflower oil; or mixed directly in a molten state with the wax.

According to a preferred embodiment, the resins are in a weight percentage not exceeding 45%, and preferably 15 to 25%, of the total composition, and most preferably in a percentage of 19%.

According to another preferred embodiment, polyvalent metal ions are selected from the group consisting of oxides, hydroxides, and salts of calcium, barium, silicon, titanium, zinc, aluminium, cobalt, iron or nickel. Preferably the ions are selected from aluminium hydroxide, titanium dioxide, silicon dioxide. According to another preferred embodiment, the ions are in a percentage equal to or less than 10% by weight of total composition, preferably 1%.

Optionally, in another preferred embodiment, the binder composition comprises additives for increasing the open time, opacity, hardness and water resistance, to increase the ease of handling of paint, to reduce surface defects, such as craters, fish eyes, orange peel, telegraphing, pinholes, floating and silking, to facilitate the application of the paint, and to increase its drying time.

According to a preferred embodiment, the additives to increase opacity, hardness and water resistance are selected from the group consisting of inert pigments such as calcium carbonate, aluminium silicate, silicon dioxide, barium sulfate or magnesium carbonate.

According to another preferred embodiment, additives to increase the hardness and water resistance are selected from the group consisting of drying oils such as linseed, walnut, poppy, perilla and tung oils.

In another preferred embodiment, the additives to increase the open time of the paint is selected from the group consisting of glycerol, cellulose esters, glycols, polyoxyethylene fatty alcohols, soybean lecithin or low viscosity oils.

In another preferred embodiment, the additives to increase the paint's ease of handling are selected from polyphosphates and polyacrylic and polyurethane dispersants.

In another preferred embodiment, additives to reduce surface defects are selected from defoamers based on silicone or mineral or fatty oils, hydrophobic salts and metal salts.

In another preferred embodiment, additives to reduce surface defects are selected from modified polydimethyl siloxanes and polymethyl siloxanes or polyacrylates.

Thus this first aspect of the present invention relates to a binder composition for the manufacture of paints and inks, wherein said paints and inks are intended for artists, for school use, for printing inks used in screen printing, lithography and etching, and as decorative paint for exterior and interior walls.

A second aspect of the invention relates to a manufacturing method of the paint binder composition, comprising the following stages:

a) melting of wax to a temperature range between 65 and 90° C.;
b) mixing of an emulsifying agent, a curing agent and a drying oil at a temperature range between 15 and 25° C.;
c) mixing of the emulsifying agent, the curing agent and the drying oil from step b) with water;
d) mixing of the molten wax from step a) with the mixture obtained in step c) to a temperature range of between 65 and 90° C.;
e) cooling of the mixture obtained in step d) to a temperature of 15 to 25° C.;
f) adding to the mixture from step e) at room temperature a resin and polyvalent metal ions.

According to another preferred embodiment, after step e), additives are added. Such additives are the same additives as described above.

Once the the binder composition is prepared as described above, the pigment to be used is added, in powder form or as liquid colorant.

If the pigment is in powder form, the mixture is ground in a mill.

If the pigment is in the form of liquid colorant, it is mixed with the binder composition by means of a high speed disperser.

Once the mixture of the binding composition and the pigment has been carried out, a paint ready for filtering and filling is obtained.

A third aspect of the present invention relates to a paint comprising a binder composition as defined above.

A fourth aspect of the present invention relates to the use of the binder composition for paints and inks.

In the present invention, drying oil is understood to be an oil that hardens and produces a tough and strong film after being exposed to air for some time. Examples of drying oils, not limited to but merelly illustrative, are linseed oil, tung oil, poppyseed oil, perilla oil and walnut oil.

Throughout the description and claims, the word "comprise" and its variations are not intended to exclude other technical features, components or steps. For the experts in the field, other purposes, advantages and features of the invention will become apparent partly from the description and partly from the practice of the invention. The following examples are provided by way of illustration and are not intended to be limiting of the present invention.

EXAMPLES

Below some examples of application of the procedure are described, provided by way of illustration and not intended to be limiting of the present invention.

Example 1

Preparation of a Binder Composition

For the manufacture of the binder composition, bleached beeswax in the amount of 600 g is melted at a temperature of 70° C. Then an emulsifying agent of potassium oleate, a curing agent of aluminium stearate, and a drying oil of bleached linseed oil in amounts of 300 g, 100 g, and 100 g respectively, are mixed at a temperature of 18° C.

Following this step, the emulsifying agent, the curing agent, and the drying oil, previously mixed, are mixed with 180 ml of water.

Then the molten wax and the mixture previously obtained are mixed at a temperature of 70° C.

The mixture is set to cool to a temperature of 18° C.

Finally, 300 g of acrylic resin emulsion and 25 g of polyvalent metal ions of aluminium hydroxide are added at 18° C. to the mixture obtained in the previous step.

Thus is obtained a binder composition comprising the following elements:
bleached beeswax 37.4%
potassium oleate 18.7%
acrylic resin emulsion 18.7%
aluminium stearate 6.2%
bleached linseed oil 6.2%
aluminium hydroxide 1.5%
water 11.3%

The invention claimed is:

1. A paint comprising a binder composition comprising the following elements:
   a) beeswax;
   b) potassium soaps of a fatty acid selected from oleic, linoleic or linoleic acid or a combination thereof;
   c) curing agents selected from the group consisting of calcium oleate, aluminum oleate, calcium stearate, aluminum stearate, barium stearate, magnesium palmitate, zinc resinate, calcium resinate and manganese resinate, or any combination thereof;
   d) drying oils selected from linseed oil, walnut oil and poppyseed oil, in a weight percentage not exceeding 20% with respect to the total composition;
   e) resins selected from the group consisting of acrylic resins, dammar, and any combination thereof, in a weight percentage not exceeding 45% of the total composition;
   f) polyvalent metal ions selected from aluminum and calcium hydroxides or titanium and silicon dioxides in a percentage equal to or less than 10% of the total composition; and
   g) water.

2. The paint according to claim 1, wherein the beeswax is in a weight percentage of 20 to 55% of the total binder composition.

3. The paint according to claim 1, wherein the beeswax is in a weight percentage of between 33 to 50% of the total binder composition.

4. The paint according to claim 1, wherein the oleic, linoleic or linolenic acid or combination thereof are in a proportion exceeding 40% of the fatty acid content in the potassium soap.

5. The paint according to claim 1, wherein the potassium soap is selected from potassium oleate or potassium linoleate.

6. The paint according to claim 1, wherein the potassium soap is in a weight percentage of 2 to 45% of the total binder composition.

7. The paint according to claim 1, wherein the potassium soap is in a weight percentage of 15 to 25% of the total binder composition.

8. The paint according to claim 1, wherein the potassium soap is in a weight percentage of 19% of the total binder composition.

9. The composition according to claim 1, wherein the resins are in emulsion; in dispersion; dissolved in organic solvents, preferably turpentine, or white spirit or mixed directly in a molten state with the wax.

10. The paint according to claim 1, wherein the resins are in a weight percentage of 15 to 25% of the total binder composition.

11. The paint according to claim 1, wherein the resins are in a weight percentage of 19% of the total binder composition.

12. The paint according to claim 1, wherein the polyvalent metal ions are in a percentage of 1% by weight of total binder composition.

13. The paint according to claim 1, wherein the binder composition optionally comprises additives selected from the group consisting of glycerol, cellulose esters, glycols, polyoxyethylene fatty alcohols, soybean lecithin, low viscosity oils, calcium carbonate, aluminum silicate, silicon dioxide, barium sulfate, magnesium carbonate.

14. A manufacturing process of the paint of claim 1 which comprises the following steps:
   a) melting of beeswax to a temperature range between 65 and 90° C.;
   b) mixing at a temperature range between 15 and 25° C. of:
   potassium soap of fatty acids selected from oleic, linoleic, linolenics or any combination thereof;
   a curing agent selected from the group consisting of calcium oleate, aluminum oleate, calcium stearate, aluminum stearate, barium stearate, magnesium palmitate, zinc resinate, calcium resinate and manganese resinate or combination thereof;
   and a drying oil selected from linseed oil, walnut oil and poppyseed;
   c) mixing of the potassium soap, the curing agent, and the drying oil from step b) with water;
   d) mixing of the molten beeswax from step a) with the mixture obtained in step c) at a temperature range between 65 and 90° C.;
   e) cooling of the mixture obtained in step d) at a temperature of 15 to 25° C.;
   f) optionally, adding additives selected from the group consisting of glycerol, cellulose esters, glycols, polyoxyethylene fatty alcohols, soybean lecithin, low viscosity oils, calcium carbonate, aluminium silicate, silicon dioxide, barium sulfate, magnesium carbonate to the mixture of step e);
   g) adding to the mixture from step e) at room temperature a resin selected from the group consisting of acrylic resins, and dammar, and polyvalent metal ions selected from aluminum and calcium hydroxides or titanium and silicon dioxides; and
   h) mixing the composition obtained in step g) with a pigment.

* * * * *

UNITED STATES PATENT AND TRADEMARK OFFICE
CERTIFICATE OF CORRECTION

PATENT NO. : 9,062,215 B2  
APPLICATION NO. : 14/116740  
DATED : June 23, 2015  
INVENTOR(S) : Jorge Cuní Bravo et al.

Page 1 of 1

It is certified that error appears in the above-identified patent and that said Letters Patent is hereby corrected as shown below:

IN THE CLAIMS

Column 5, Claim 1, line 21, delete "or linoleic acid" and insert --or linolenic acid--

Signed and Sealed this  
Ninth Day of February, 2016

Michelle K. Lee  
*Director of the United States Patent and Trademark Office*